(12) United States Patent
Mermillod-Ansleme et al.

(10) Patent No.: US 11,600,962 B2
(45) Date of Patent: Mar. 7, 2023

(54) DEVICE FOR COOLING LOCALLY

(71) Applicant: Commissariat a l'energie atomique et aux energies alternatives, Paris (FR)

(72) Inventors: Quentin Mermillod-Ansleme, Grenoble (FR); Nicolas Aubert, Grenoble (FR); Claude Chabrol, Grenoble (FR); Mathieu Dupoy, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 561 days.

(21) Appl. No.: 16/774,131

(22) Filed: Jan. 28, 2020

(65) Prior Publication Data
US 2020/0244033 A1    Jul. 30, 2020

(30) Foreign Application Priority Data
Jan. 29, 2019 (FR) ...................... 19 00768

(51) Int. Cl.
*A61F 7/00* (2006.01)
*H01S 3/16* (2006.01)
(Continued)

(52) U.S. Cl.
CPC ............ *H01S 3/1653* (2013.01); *A61F 7/007* (2013.01); *H01S 3/0405* (2013.01); *A61F 2007/0002* (2013.01); *A61F 2007/126* (2013.01)

(58) Field of Classification Search
CPC ...... A61F 2007/0002; A61F 2007/0088; A61F 2007/0096; A61F 2007/126; A61F 7/007;
(Continued)

(56) References Cited

U.S. PATENT DOCUMENTS

| 5,447,032 A | * | 9/1995 | Epstein | ................. | F25B 23/003 |
| | | | | | 62/3.1 |
| 6,041,610 A | * | 3/2000 | Edwards | ............... | F25B 23/003 |
| | | | | | 62/3.1 |

(Continued)

FOREIGN PATENT DOCUMENTS

| EP | 2 717 029 A2 | 4/2014 |
| FR | 3 055 796 A1 | 3/2018 |

(Continued)

OTHER PUBLICATIONS

French Preliminary Search Report dated Nov. 14, 2019 in French Application 19 00768 filed on Jan. 29, 2019 (with English Translation of Cited Documents & Written Opinion), 10 pages.

*Primary Examiner* — Tigist S Demie
(74) *Attorney, Agent, or Firm* — Oblon, McClelland, Maier & Neustadt, L.L.P.

(57) ABSTRACT

A device for cooling locally, including a cooling member, a crystal having the capacity to cool via absorption of a near-infrared exciting light signal, an illuminating system intended to deliver an exciting light signal, the crystal having an elongate shape about a longitudinal axis between a near end and a far end and having a closed constant outside cross section and containing a central channel formed, from its far end, over at least some of its length, the cooling member including a rod embedded via a first end into the central channel of the crystal and including a protruding second end that forms a cooling finger.

16 Claims, 9 Drawing Sheets

(51) Int. Cl.
*H01S 3/04* (2006.01)
*A61F 7/12* (2006.01)

(58) Field of Classification Search
CPC ......... A61F 7/12; G02B 5/001; H01S 3/0405; H01S 3/0408; H01S 3/1618; H01S 3/1653
See application file for complete search history.

(56) References Cited

U.S. PATENT DOCUMENTS

| | | | |
|---|---|---|---|
| 6,378,321 | B1 | 4/2002 | Epstein et al. |
| 7,204,833 | B1 * | 4/2007 | Osorio ................. A61B 5/4094 607/105 |
| 2009/0052482 | A1 | 2/2009 | Vermeulen et al. |
| 2014/0094792 | A1 | 4/2014 | Sharonov |
| 2016/0287225 | A1 | 10/2016 | Sharonov |

FOREIGN PATENT DOCUMENTS

| | | |
|---|---|---|
| JP | 11-153754 A | 6/1999 |
| WO | WO 2007/104506 A2 | 9/2007 |

\* cited by examiner

DEVICE FOR COOLING LOCALLY

TECHNICAL FIELD OF THE INVENTION

The present invention relates to a device for cooling locally, notably an organ, such as for example the human brain.

PRIOR ART

It is known to treat certain diseases by cooling tissues locally. This is for example the case for diseases, such as epilepsy, in which localized cooling of the epileptogenic zone allows the onset of seizures to be blocked or their propagation to be limited. This is of interest to patients afflicted with this pathology and who cannot be treated, because of drug resistance, with conventional medicines. However, cooling devices are often not very suitable for chronic intra-cerebral implantation. Certain known solutions, which are not suitable for implantation, are for example based on microfluidic coolers or thermoelectric coolers using the Peltier effect.

Various solutions are described in the documents referenced US2007/005121A1, JP2006/015064A, U.S. Pat. Nos. 5,620,571A, 9,362,712B1, WO2016/102351A1.

Moreover, another cooling technology consists in employing a crystal capable of cooling when it is excited by a laser beam.

The cooling crystal is preferably formed from a material able to exhibit the physical phenomenon referred to as anti-Stokes fluorescence. This phenomenon consists of inelastic scattering of light, involving an exchange of energy between an incident photon of defined wavelength and the crystal lattice. The light scattered by the crystal thus does not have the same wavelength as the incident light. In the case of an anti-Stokes shift, the scattered light has a shorter wavelength than the incident light and therefore a higher energy, this leading to cooling of the crystal. Devices using this cooling mechanism have notably been described in patent U.S. Pat. No. 6,041,610 and in patent applications WO00/42683A1 and WO2018/051005A1.

The solutions proposed in the patent documents referenced above are unsatisfactory, notably from the point of view of cooling efficiency and from the point of view of the ratio between compactness and cooling efficiency.

The aim of the invention is to provide a device for cooling locally that has an increased efficiency and a particularly compact design.

SUMMARY OF THE INVENTION

This aim is achieved by a device for cooling locally, comprising:
- a cooling member,
- a crystal having the capacity to cool via absorption of a near-infrared exciting light signal,
- an illuminating system intended to deliver an exciting light signal,
- said crystal having an elongate shape about a longitudinal axis between a near end and a far end and having a closed constant outside cross section and containing a central channel formed, from its far end, over at least some of its length,
- said cooling member comprising a rod embedded via a first end into said central channel of said crystal and comprising a protruding second end that forms a cooling finger, the illuminating system being configured to generate said exciting light signal with an annular shape.

According to one particularity, the crystal has a constant cross section of annular shape between its near end and its far end.

According to another particularity, the illuminating system comprises a light source configured to emit a first light signal and a shaping module for shaping said first light signal arranged between said light source and the near end of said crystal and configured to generate said exciting signal with the annular shape.

According to another particularity, the shaping module comprises a first axicon lens and a second axicon lens.

According to another particularity, the crystal is of Yb:YLF or Tm:Yb:YLF.

According to another particularity, the finger of the cooling member has an atraumatic shape.

Advantageously, the device comprises means for recycling the fluorescence generated during the excitation of said crystal.

According to one particularity, said crystal comprises a lateral surface and said means for recycling the fluorescence comprise one or more dichroic filters that are arranged on the periphery of said lateral surface of the crystal, and that form a lateral covering of said crystal, said covering being thermally insulated from the lateral surface of the crystal.

Advantageously, the means for recycling the fluorescence comprise fluorophore elements.

Advantageously, said covering comprises at least two dichroic filters and fluorophore elements are arranged between the two dichroic filters.

According to one particularity, said covering is composed of a single-piece cylinder or of a plurality of adjacent sheets that are assembled with one another in a continuous way.

According to one particularity, the device comprises means for fastening said covering.

According to a first particular embodiment, the fastening means comprise a washer bearing said covering and slipped around the rod of the cooling member.

According to one particularity, the washer has a face located facing the crystal, on which face is deposited a coating made of reflective material.

According to a second particular embodiment, said fastening means comprise one or more annular spacers that are positioned around the lateral surface of said crystal and that hold said covering.

According to one particularity, each spacer comprises a plurality of flexible strips that bear against the lateral surface of said crystal.

BRIEF DESCRIPTION OF THE FIGS

Other features and advantages will become apparent from the detailed description, which is given with reference to the appended drawings, in which.

DETAILED DESCRIPTION OF AT LEAST ONE EMBODIMENT

Figure 1A:
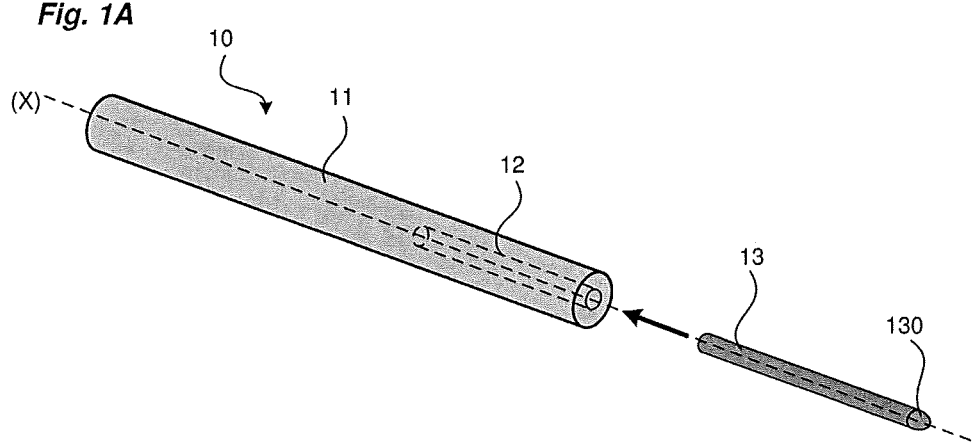
FIGS. 1A and 1B illustrate, seen in perspective, a principle of production of the probe of the device for cooling locally according to the invention.

The invention relates to a device for cooling locally, notably an organ, with a view to cooling the tissues thereof. Said organ will for example be the human brain.

Nonlimitingly, the device of the invention will for example be suitable for treating various pathologies, for example:
Epileptic seizures,
Cranioencephalic trauma,
Neuro-Cancer,
Parkinson's disease or other movement disorders such as dystonia, essential tremors, Huntington's disease.

Of course, given certain adaptations, it will be understood that the device will possibly be employed to treat other pathologies.

In the case of treatment of an epileptic seizure, the source of generated cold is intended to be placed in contact with epileptogenic foci or with any other zone of the brain 30 that is surgically accessible using stereotactic mini-invasive methods via a cranial drill hole of a few millimeters. The cooling generated then contributes to stoppage of the seizure or to blockage of the onset thereof.

It is possible for other applications to be envisioned, notably in the field of space technology (cooled infrared imaging) or in the field of cooled spectrometry.

For a medical application, the device 1 for cooling locally according to the invention comprises a biocompatible probe 10 that is implantable so as to be able to act on command at any time, for example when the onset of an epileptic seizure is detected, using algorithms for detecting seizures in a closed-loop mode.

In the targeted application, detecting means 20, which are not the subject of the present patent application, are for example employed to detect the onset of the pathology to be treated. In the case of an epileptic seizure, these detecting means 20 are implanted in the skull (brain 30 in FIG. 2A for example) in order to monitor an epileptogenic zone. When the onset of a seizure is detected, the detecting means 20 send a signal S1 to a processing and control unit UC. The processing and control unit UC then transmits in response a suitable command (S2) to the probe 10 of the device. The cooling device of the invention is controlled to generate cooling that is suitable for the treated pathology. If it is a question of an epileptic seizure, the intensity of the cooling and its duration of application will preferably be related to the intensity level of the seizure, which will have been measured by the detecting means 20. To generate a command that is suitable for the cooling device, the processing and control unit UC preferably comprises an analyzing module that is intended to analyze the signal S1 received from the detecting means and to determine a suitable treatment.

The processing and control unit UC advantageously forms part of the cooling device 1 of the invention. It comprises at least one microprocessor and a memory. It is intended to execute software instructions that are representative of a sequence of treatment of the pathology by the device. It notably comprises means for controlling an illuminating system 14 that will be detailed below. It also comprises one or more communication interfaces that are intended to communicate with various entities, notably the detecting means described above. The communication links will possibly be wired or wireless.

The probe 10 of the cooling device 1 of the invention comprises a cooling crystal 11. The cooling crystal 11 is preferably formed from a material able to exhibit the physical phenomenon referred to as anti-Stokes fluorescence. This phenomenon consists of inelastic scattering of light, involving an exchange of energy between an incident photon of defined wavelength and the crystal lattice. The light scattered by the crystal thus does not have the same wavelength as the incident light. In the case of an anti-Stokes shift, the scattered light has a shorter wavelength than the incident light and therefore a higher energy, this leading to cooling of the crystal.

Nonlimitingly, the employed crystal will preferably be formed from any host matrix that is transparent in the near infrared (900-1100 nm) and that has low-energy phonons. This matrix will preferably be doped with ytterbium ions ($Yb^{3+}$). It will for example be a crystal type of 10% wt. Yb:YLF. Its excitation wavelength is comprised between about 1010 nm and 1040 nm, and is preferably 1020 nm.

Of course, any other crystal composition may be envisioned, such as for example that of a crystal of YLF co-doped with 5% Yb and 0.0016% Tm. Generally, ions of any of the lanthanides may be envisioned. Particular attention will be paid to the purity of the crystals used. For example, components of 5N purity will be used during the manufacture of the host matrix.

In the case of a crystal doped with ytterbium, the cooling principle is as follows and has already been described in patent application WO2018/051005A1 and illustrated in patent application US2017/0137684A1: let an electron initially be in level E4. This electron is raised to an excited state E5 by absorbing an incident photon of 1020 nm wavelength. It is then raised to higher energy states (E6, E7) by absorbing acoustic phonons of the crystal lattice. This electron decays radiatively to the fundamental energy levels (E1-E4) by emitting a photon of average fluorescence wavelength (about 990 nm). Another phonon is absorbed to return the electron to its equilibrium state.

Figure 1B:
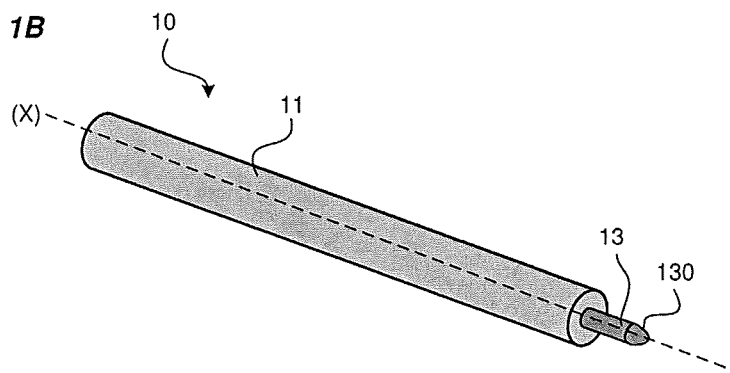
Figure 2A:
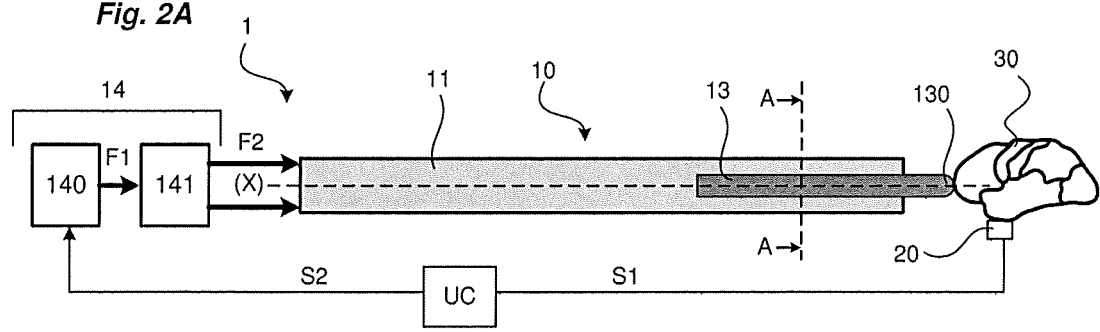
FIG. 2A shows, schematically via a longitudinal cross-sectional view, the device for cooling locally according to the invention and illustrates its operating principle.
Figure 2B:
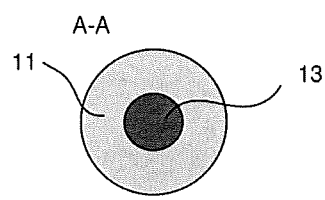
FIG. 2B shows the probe of the device of the invention, seen via the enlarged transverse cross section A-A.

According to one particularity of the invention, with reference to FIGS. 1A and 1B and to FIGS. 2A and 2B, the crystal 11 is produced with a shape that is elongate along a longitudinal axis (X), between a near end that receives first an exciting light signal and a far end that is able to be located as close as possible to the organ 30 to be treated. The crystal 11 has a closed constant outside transverse cross section and, along its longitudinal axis, a hollow central space creating a channel 12 produced over all or some of its length and thus defining a cylindrical internal heat-exchange surface.

Advantageously, the transverse cross section of the crystal 11 is thus of annular shape at least over the segment of length including the central channel 12.

The probe also comprises a cooling member 13 having an external surface that makes mechanical contact with the internal surface of the crystal. The cooling member 13 is intended to capture the negative temperature variation generated by the cooling crystal when the latter is suitably excited.

According to one particularity, this cooling member 13 has an elongate structure between a first end and a second end. It comprises an axisymmetric cylindrical rod that is embedded, via its first end, into said central channel 12 of the crystal 11, and a cooling finger 130 (also called the "cold finger") of atraumatic shape located at the second end of said rod. The cooling member 13 is advantageously held only by the mechanical joint formed when it is embedded into the central channel 12 of the crystal 11.

The cooling member 13 is advantageously made of sapphire, this material having a high thermal conductivity, a suitable level of transparency in the near infrared and biocompatibility characteristics.

The rod of the cooling member may be inserted axially into the channel over the entire length of the channel up to abutment when the channel is blind, so that only the cooling finger 130 protrudes with respect to the far end of the crystal 11.

Once the cooling member 13 has been embedded, the outside lateral surface of the rod makes mechanical contact with the inside surface of the crystal 11, allowing heat exchange between the two elements.

The cooling finger 130 is intended to make contact with the organ to be cooled (brain 30 in FIG. 2A).

Figure 4:
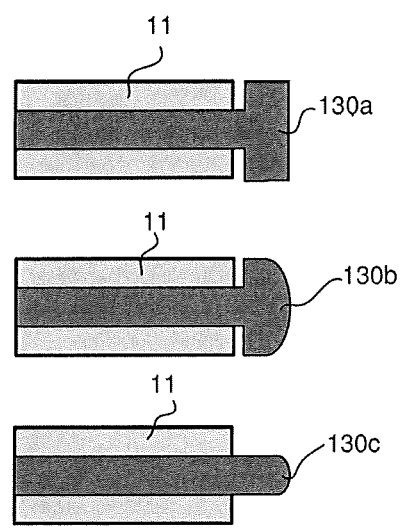
FIG. 4 shows a plurality of possible configurations of the cooling finger employed in the device according to the invention.

With reference to FIG. 4, at its end, the finger 130 may for example have a flared T shape (130a) or a mushroom shape (130b) or a straight rod-like shape (130) ending in a rounded dome. Other atraumatic shapes may be envisioned.

According to one particularity of the invention, the device 1 comprises an illuminating system 14 comprising at least one source 140 intended to generate a light signal. The signal is employed to excite the crystal according to the principal described above.

The illuminating system is configured to generate an exciting signal having a ring-shaped transverse cross section in order to excite only the crystal, this cross section advantageously being identical or at least inscribed in the transverse cross section of the crystal 11 so as to not excite the central channel 12 of the crystal 11 in which the cooling member 13 is located. The illuminating system thus comprises means for generating this exciting signal of annular transverse cross section.

Nonlimitingly, the exciting signal may thus be obtained by virtue of a light source that naturally delivers an exciting signal of annular cross section.

As a variant, the light source 140 is advantageously a laser that generates a Gaussian beam. In this case, it turns out that embedding the cooling member 13 into the crystal 11 prevents Gaussian excitation of the crystal because the entirety of the laser power is then guided axially toward the cooling member 13, right up to the zone to be cooled. According to one particularity, the illuminating system 14 of the device thus comprises a module 141 for shaping the Gaussian beam F1 emitted by the laser into a beam F2 of constant annular cross section that thus allows only the crystal 11 to be excited. The beam F2 of annular cross section that is generated advantageously has a transverse cross section that is identical or at least inscribed in the transverse cross section of the crystal 11, so as to not excite the central channel 12 of the crystal 11 in which the cooling member 13 is located, and to concentrate the power of the laser on the crystal 11 located peripherally thereto.

Figure 3:
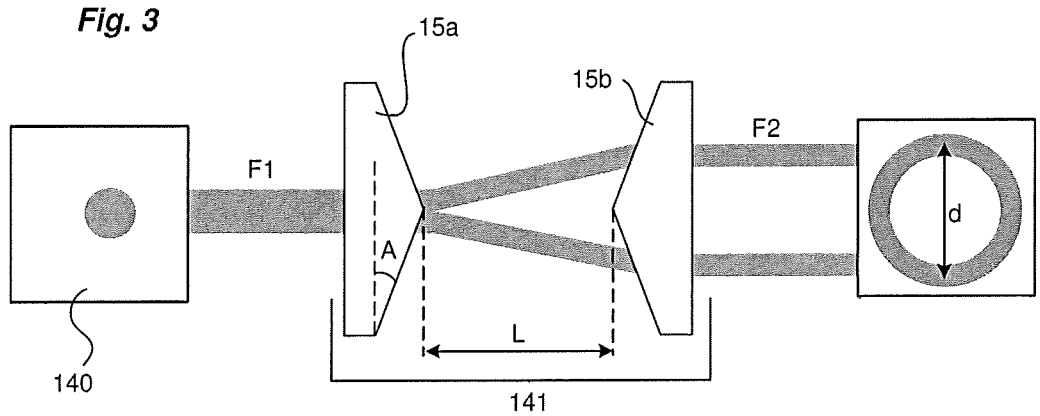
FIG. 3 illustrates the principle of production of the exciting light signal employed in the device according to the invention.

As shown in FIG. 3 and nonlimitingly, the module 141 for shaping the Gaussian beam of the laser may comprise two axicons 15a, 15b in series, back-to-back and the apexes of which are separated by a nonzero distance L. Each axicon may be formed from a lens of conical shape the angle A of which will be suitably chosen. The use of an axicon doublet is advantageous in its ease of implementation and its flux resistance. The diameter of the annulus obtained as output from the shaping module is $d=2 \times L \times \tan(A(n-1))$ and proves to be easily adjustable by changing the distance L between the apexes of the two lenses and the angle A of each lens.

Of course, the shaping module 141 could take another form. By way of example, the axicons could be replaced by a phase delay plate.

Advantageously, to improve the efficiency of the device and of its probe, it is possible to employ means for recycling the fluorescence generated by exciting the crystal 11 with the light signal.

It will be seen below that these recycling means integrated into the probe are advantageously formed from one or more dichroic filters 16 arranged around the crystal 11 in the form of a lateral covering and allowing the low-energy fluorescence photons (by "low-energy", what is meant is lower than the average fluorescence energy) to be recycled by reflecting them toward the crystal 11. By virtue of these means, 50% of the fluorescence is reabsorbed by the crystal 11, this allowing the cooling efficiency to be doubled and the harmful fluorescence of the crystal to be divided by two. Moreover, the cooling speed of the crystal 11 is increased.

The principle of the invention resides in recycling fluorescence photons of energies lower than the average fluorescence energy, which is defined as:

$$h\nu_f = \frac{hc}{\lambda_f}$$

where
h is Planck's constant,
$\nu_f$ is the average frequency of the fluorescence photons, and
c is the speed of light under vacuum.
For its part, $\lambda_f$ is the average wavelength of the fluorescent photons, such that:

$$\lambda_f = \frac{\int \lambda S(\lambda) d\lambda}{\int S(\lambda) d\lambda}$$

where S is an experimentally measured quantity corresponding to an emission spectral density (number of photons emitted per wavelength interval).

Figure 9:
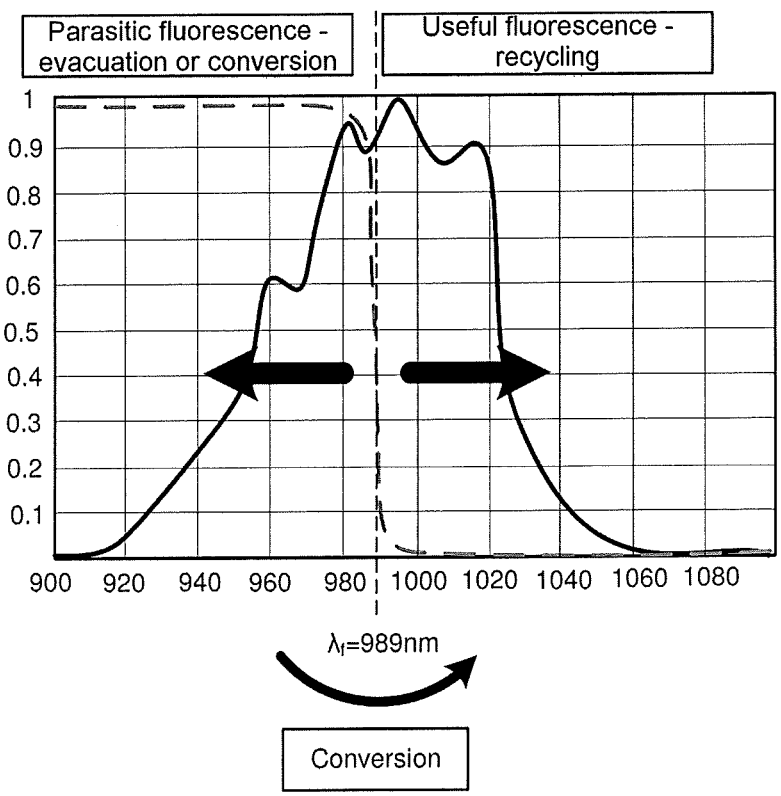
FIG. 9 shows the spectrum of the fluorescence emitted by the crystal employed in the device of the invention.

FIG. 9 illustrates a normalized fluorescence spectrum for a crystal of 10% wt. $Yb^{3+}$:YLF. For this crystal, the measured average fluorescence wavelength is $\lambda_f$=989 nm. This wavelength corresponds to a cooling efficiency (i) of zero, the cooling efficiency being defined by the following equation:

$$\eta_c(\lambda, T) = \frac{P_{cool}}{P_{aBA}} = 1 - \eta_{ext}\left(\frac{\alpha_r(\lambda, T)}{\alpha_r(\lambda, T) + \alpha_b}\right)\frac{\lambda}{\lambda_f(T)}$$

where $\eta_{ext}$ is the external quantum efficiency, $\alpha_r(\lambda,T)$ is the resonant absorption, which is dependent on the excitation wavelength and on temperature, and $\alpha_b$ is the residual absorption caused by the presence of impurities in the crystal.

The principal thus consists in using a wavelength-selective dichroic filter 16 (ideal filter illustrated by the dashed line in FIG. 9) that, in the ideal case, allows fluorescence photons of wavelengths longer than $\lambda_f$, which will be able to be reabsorbed by the crystal 11 and thus to increase the cooling efficiency, to be reflected. The wavelengths transmitted by the filters 16 are those the wavelengths of which are shorter than $\lambda_f$.

Figure 5A:
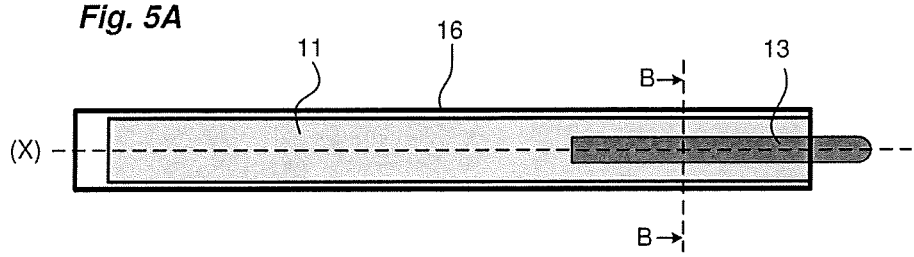
FIG. 5A illustrates, schematically via an axial longitudinal cross-sectional view, a principle of production of the probe of the device for cooling locally according to the invention.
Figure 5B:
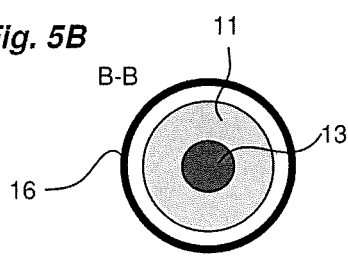
FIG. 5B shows the probe of the device of the invention, seen via the enlarged transverse cross section B-B and shows the dichroic-filter covering produced with a circular cross section.
Figure 5C:
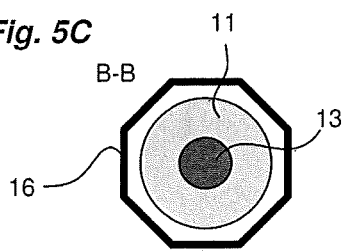
FIG. 5C shows the probe of the device of the invention, seen via the enlarged transverse cross section B-B and shows the dichroic-filter covering produced with an octagonal cross section.

As shown in FIGS. 5A to 5C, the dichroic filters 16 of the device 1 are assembled into the form of a lateral covering arranged around the lateral surface of the crystal 11, coaxially with respect to said surface, and in such a way as to not make contact with said surface. The covering may take the form of a single-piece cylindrical tube or of a plurality of sheets that are assembled with one another contiguously. In the latter case, each sheet may be planar or curved. The assembled filters then together form a through-cylinder of prismatic shape (for example of circular outside cross section in FIG. 5B or of octagonal outside cross section in FIG. 5C) and of axis coincident with the axis (X).

To fasten the filters around the crystal, hold them in position and thus form said covering, various fastening means may be envisioned.

With reference to FIGS. 6A to 6E, a first solution for fastening the filters 16, which is particularly advantageous, consists in equipping the cylindrical covering of the device with a washer 19 or fastening ring that plugs the covering at one of its ends, thus making one of its bases. The washer 19 contains an axial aperture 190 of diameter suitable for being slipped in a tight manner about the rod of the cooling member 13. The washer 19 is slipped onto the rod from the side of the cooling finger 130. The washer is positioned at a nonzero distance from the crystal 11 and therefore does not abut against the latter, so as to prevent any parasitic heating in operation. The washer 19 bears the dichroic filters 16 and holds them solely via its mechanical joint with the rod of the cooling member 13.

Nonlimitingly, the washer 19 is made from a thermally insulating material such as glass, silicon or a material obtained using a sol-gel process.

Figure 6A:
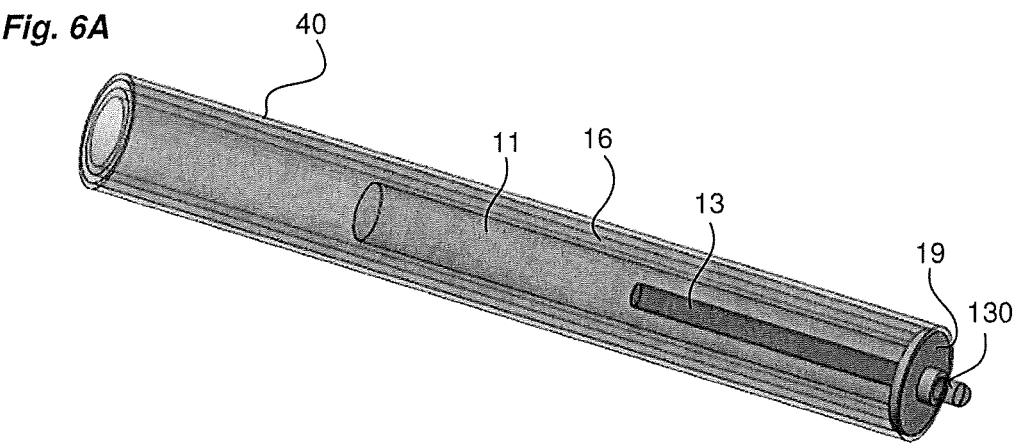
FIG. 6A shows, schematically via a perspective see-through view, the probe of the device for cooling locally of the invention, and illustrates a first solution for fastening the dichroic-filter covering.
Figure 6B:
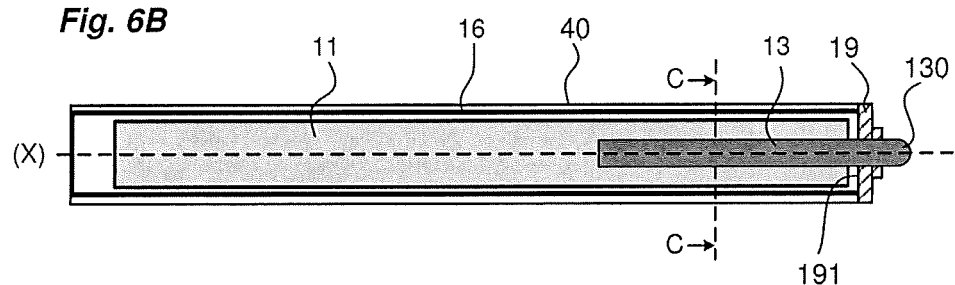
FIG. 6B shows the probe of the device of the invention of FIG. 6A, seen in axial longitudinal cross section.
Figure 6C:
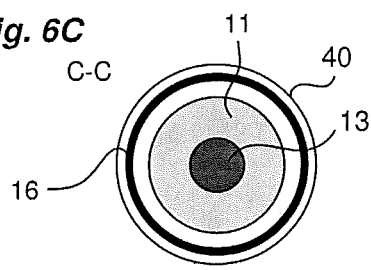
FIG. 6C shows the probe of the device of the invention, seen via the enlarged transverse cross section C-C.
Figure 6D:
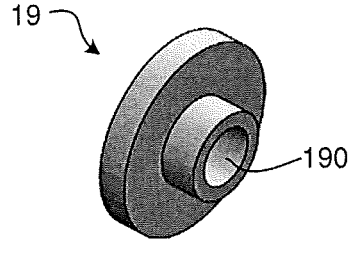
FIGS. 6D and 6E show the two faces of the washer for holding the filter covering, employed in the probe of FIGS. 6A and 6B
Figure 6E:
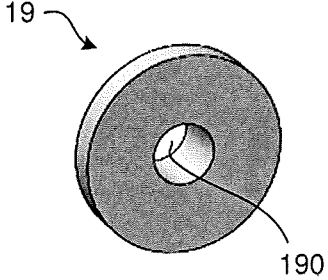
Figure 6F:
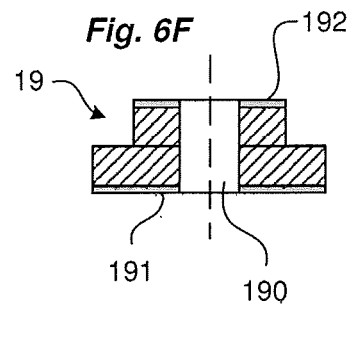
FIG. 6F illustrates one particular embodiment of the washer.

As shown in FIGS. 6D to 6F, nonlimitingly, the washer 19 may take the form of a part comprising two cylindrical segments of different diameters, making a shoulder therebetween.

Advantageously, as shown in FIG. 6F, on its face located facing the crystal 11, the washer may bear a reflective coating 191, which is for example made of gold or of silver.

Also advantageously, on the opposite face, i.e. on the face located on the side of the cold finger, the washer may bear a coating 192 made of silica ($SiO_2$—FIG. 6F) intended to form a thermal barrier and better still thermally insulate the cooling finger 130. The washer 19 may bear either of these two coatings.

This first solution for fastening the filters notably has the following advantages:
it allows any parasitic heating and losses by thermal conduction to be avoided, because neither the filter covering 16 nor the washer 19 make contact with the crystal 11; in this configuration, only the cooling member 13 makes contact with the crystal 11;
it allows constraints on the choice of the material for the fastening holder to be relaxed (in other words, it will not necessarily be necessary to employ a washer 19 made of a material that is transparent in the near infrared);
the washer 19 is easy to manufacture, for example by machining.

In FIGS. 6A to 6C, the probe also comprises an encapsulating covering 40 that is positioned around the filter covering. This encapsulating covering 40 may be employed in all the embodiments described in the present patent application.

Figure 7A:
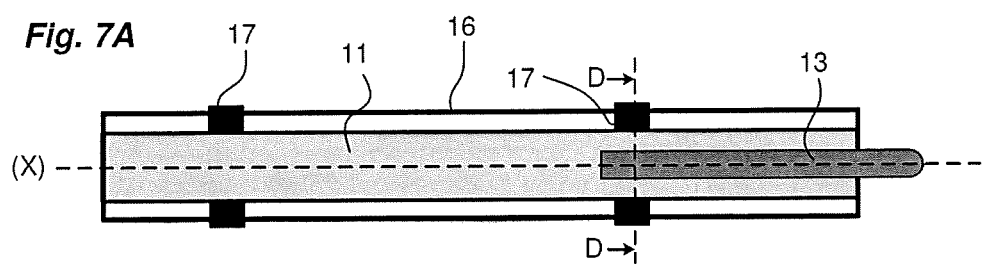
FIG. 7A shows, schematically via an axial longitudinal cross-sectional view, the probe of the device for cooling locally according to the invention, and illustrates a second solution for fastening, the dichroic-filter covering.
Figure 7B:
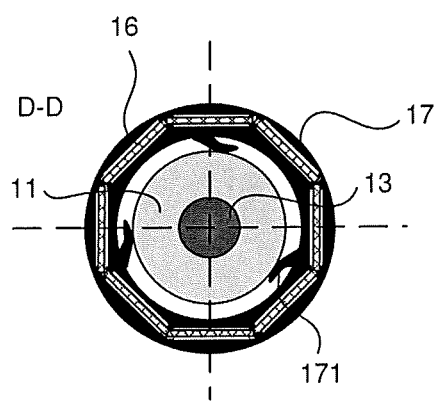
FIG. 7B shows the probe of the device of the invention, seen via the enlarged transverse cross section D-D.
Figure 8:
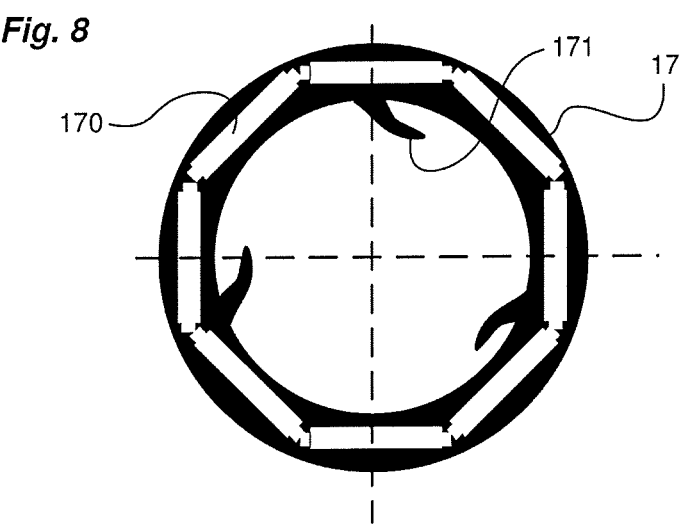
FIG. 8 shows the structure of the spacer employed in the probe of FIGS. 7A and 7B.

Another fastening solution, shown in FIGS. 7A and 7B, consists in equipping the device with one or more spacers 17 that are slipped around the cylinder formed by the crystal 11. FIGS. 7A and 7B illustrate the principle of installation of these spacers (which are for example two in number) and FIG. 8 shows a spacer in more detail. The spacers will necessarily be made from a material that is transparent in the near infrared (essentially 900-1100 nm) and that has a low thermal conductivity, in order to avoid any parasitic heating and losses by thermal conduction in operation.

The function of the spacers 17 is thus:
to position the employed dichroic filters 16 and hold the crystal 11 and each filter 16 centred with respect to each other. Each spacer 17 is provided with a plurality of apertures 170 on its perimeter in order to allow a separate filter 16 (for example taking the form of a planar or curved sheet) to be slid therein.
to allow thermo-mechanical stresses (variation in the temperature of the various elements and potential shocks) to be absorbed:

these spacers 17 are provided with flexible strips 171 (the shape is nonlimiting) the aim of which is:

to thermally insulate the crystal from the walls of the filters by limiting crystal/spacer and spacer/filter interfaces, and to allow a mechanical play of a few μm to a few hundred μm, in order to facilitate the assembly while keeping the crystal 11 centred with respect to the filters. These strips 171 are sufficiently flexible to hold the crystal by exerting a slight pressure on the latter. The surface finish of these strips 171 will be as "clean" as possible in order to avoid damage to the crystal 11 during the assembly process;

with a view to future shock-resistance tests that must be passed to meet standards, these strips 171 will be sufficiently elastic to be able to deform slightly, so as to resist thermomechanical variations due to temperature changes or shocks. For example, two spacers 17 will be positioned in order to ensure an adequate hold but also to allow resonant effects to be limited by placing these spacers asymmetrically.

Moreover, it will be noted that one of the criteria that is most important to the feasibility of a probe that is implantable into the brain is limitation of the heating of tissues to 1° C. (38° C. absolute). Numerical simulations and experimental measurements have thus been carried out in order to quantify the impact of the fluorescence on a volume of water at 37° C. The simulations and experiments have demonstrated harmful heating to greatly above 38° C. in proximity to the crystal 11 in the characteristic time taken to obtain a volume cooled below 27° C. of about one mm³. It turns out that use of dichroic filters allows this parasitic heating to be decreased by about 45%, and the volume cooled to below 27° C. to also be doubled. Moreover, the dichroic filters 16 allow the cooling rate to be increased and a cooled volume of about one mm³ to be obtained in less than 10 seconds versus 30 seconds for a probe without filters. The latter point is another criterion that is important to the feasibility of an implantable probe for cooling epileptogenic foci. Specifically, the quicker the cooled volume is achieved, the less time the epileptogenic focus has to spread and therefore the more effective the device is at treating epileptic seizures.

Figure 11A:
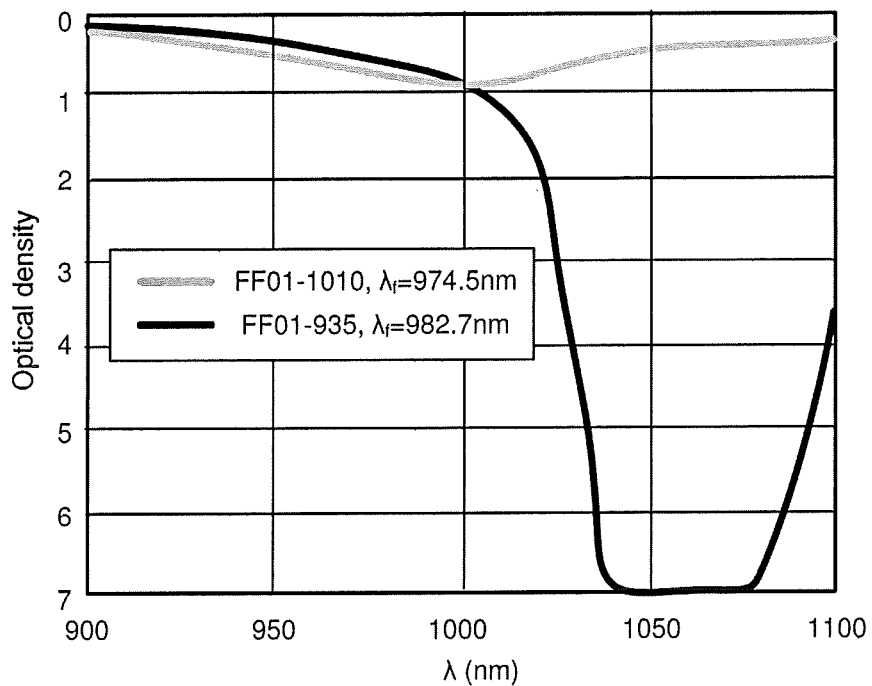
FIGS. 11A and 11B show, as a function of wavelength, a graph of optical density and a graph of absorption of the two selected dichroic filters for a solid angle of 120°, respectively.
Figure 11B:
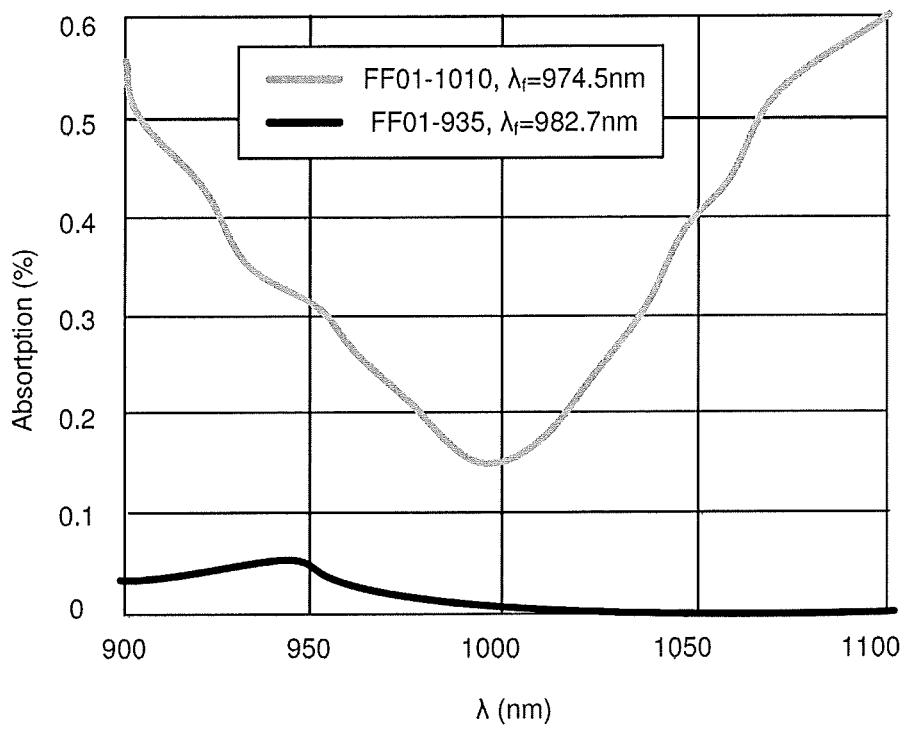

In the context of this invention, five dichroic filters of the "Semrock" brand were tested and characterized experimentally. Two filters, referenced FF01-935 and FF01-1010, were selected for their high reflectivities, even at large angles of incidence (FIG. 11A). The filter FF01-935 most particularly stands out because of its optical density higher than 7 (detection limit) at the wavelengths of interest. Moreover, the absorption of these filters at the wavelengths of fluorescence of the crystal remains lower than 1% (FIG. 11B). The parasitic heating of the filters is therefore negligible, notably with the filter FF01-935, the absorption of which is lower than 0.05%.

Figure 12A:
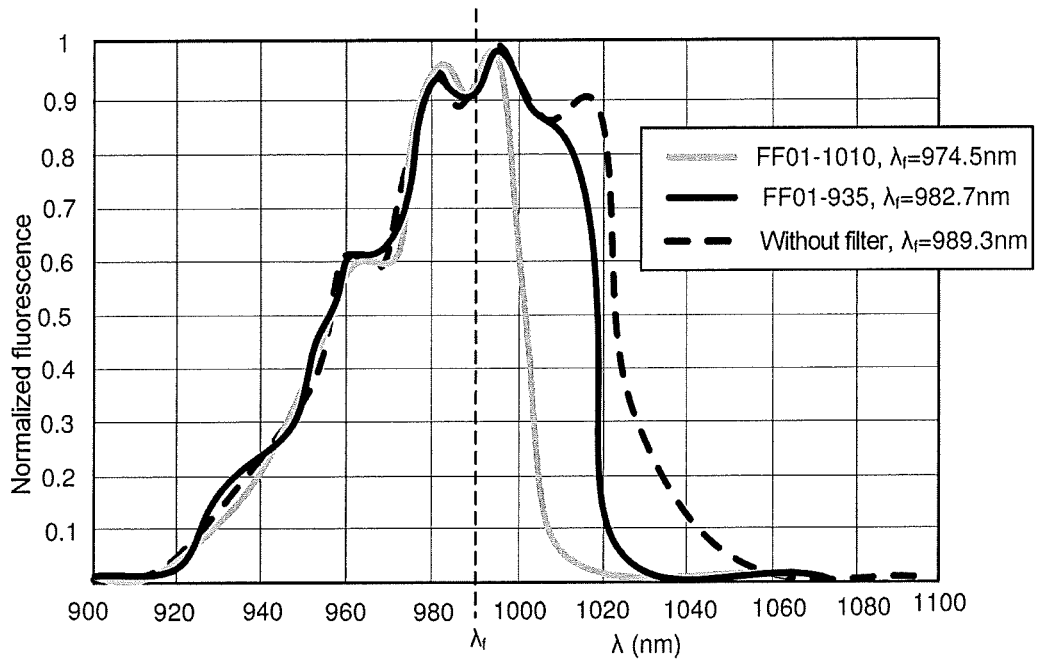
FIGS. 12A and 12B show, for a device with or without dichroic filters, a graph showing normalized fluorescence spectra at the temperature T=293 K and a graph of cooling efficiency as a function of wavelength, respectively.
Figure 12B:
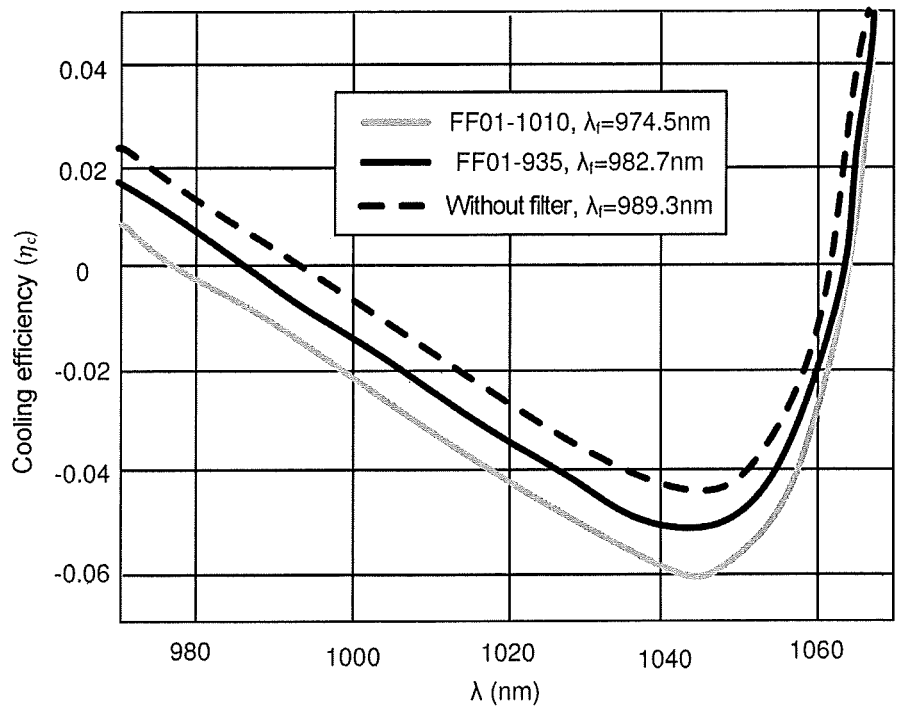

A spectral characterization of these filters was carried out on an optical test bench, the transmitted fluorescence spectra being measured with the filters positioned at about one millimetre from the surface of the crystal. This characterization allowed it to be verified that the cut-off wavelengths of the filters are beyond $\lambda_f$ (FIG. 12A). The filter FF01-1010 has the cut-off wavelength closest to this resulting in an improvement of 40% in the cooling efficiency versus 20% for the filter FF01-935 (FIG. 12B).

Figure 13A:
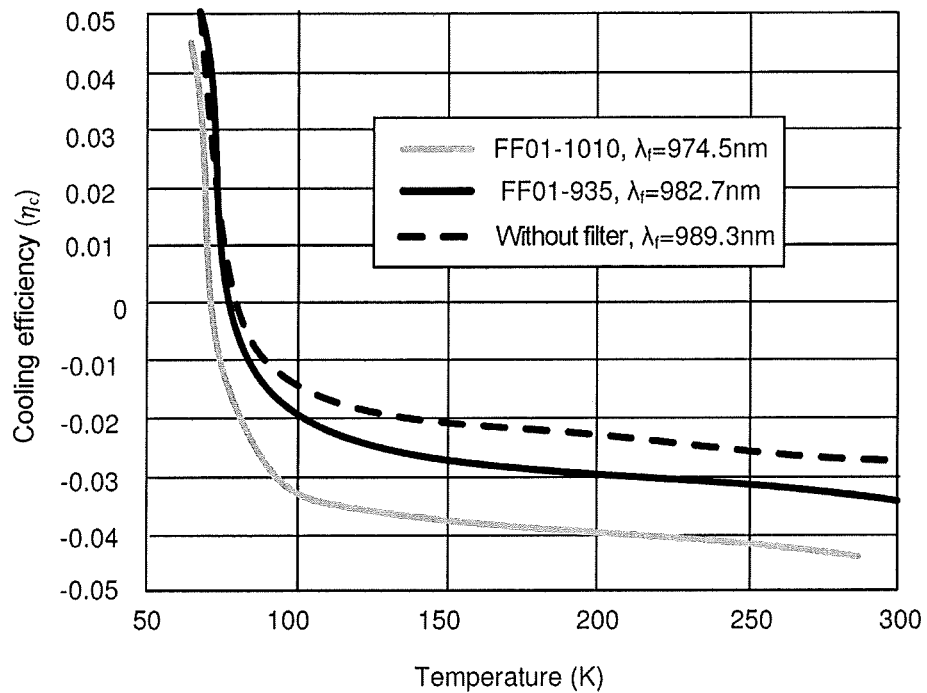
FIGS. 13A and 13B show, for a device with or without dichroic filters, a graph of the temperature dependence of the cooling efficiency and a graph of the temperature dependence of the cooling power, for an excitation at 1020 nm and a laser power of 19 W, respectively.
Figure 13B:
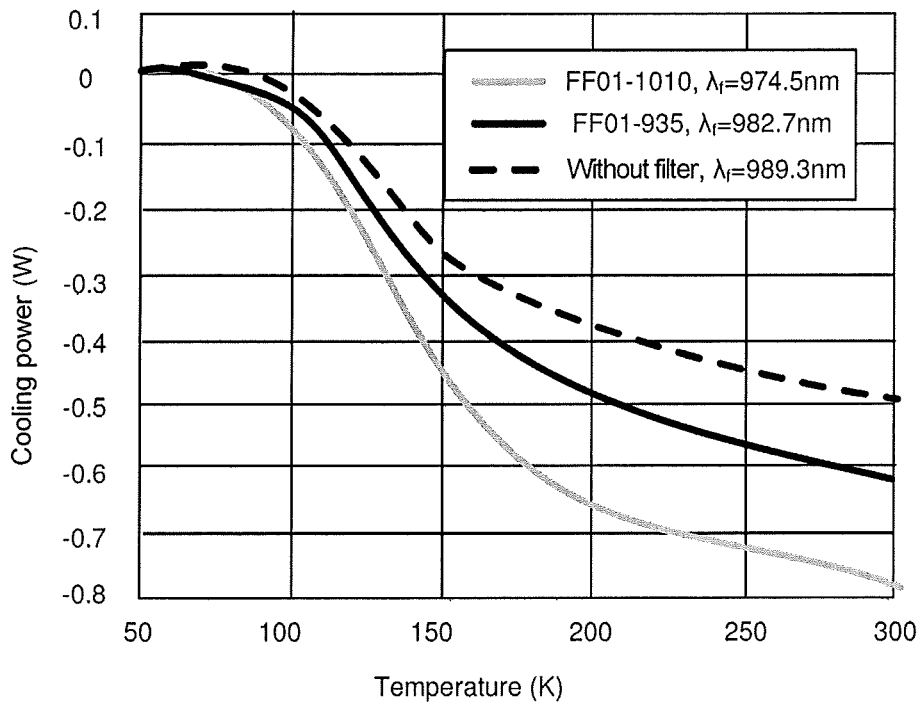

The cooling efficiency of the crystal also depends on temperature (see the equation of the cooling efficiency $\eta_c$ above). The latter decreases with temperature and becomes positive from a certain temperature corresponding to the global minimum achievable temperature (designated gMAT) of the crystal (FIGS. 13A and 13B). It will be noted that the use of dichroic filters 16 allows this temperature gMAT of the crystal to be decreased by a few degrees and the temperature of liquid nitrogen (77 K) to be reached.

Moreover, according to one particularity of the device of the invention, it is also possible to convert the wavelengths that are transmitted by the dichroic filters 16 into wavelengths useful for the cooling. Specifically, the parasitic wavelengths are of higher energies than the useful wavelengths. It is therefore easy, via a fluorescence effect, to decrease the energy of the parasitic fluorescence in order to then exploit it again.

FIG. 9 shows the spectrum of the fluorescence of the crystal 11. The right-hand portion of the spectrum is recycled by the dichroic filters 16, whereas the left-hand portion must be evacuated or recycled in order to promote cooling of the crystal. One method for converting this high-energy parasitic light into light of lower energy is to use fluorophore elements 18 the excitation spectrum of which is centred on about 970 nm and the emission spectrum of which is comprised between 1000 nm and 1060 nm. This type of fluorophore element 18 is notably employed in medical imaging applications. Specifically, this wavelength range corresponds to a window of transparency of biological tissues.

Figure 10A:
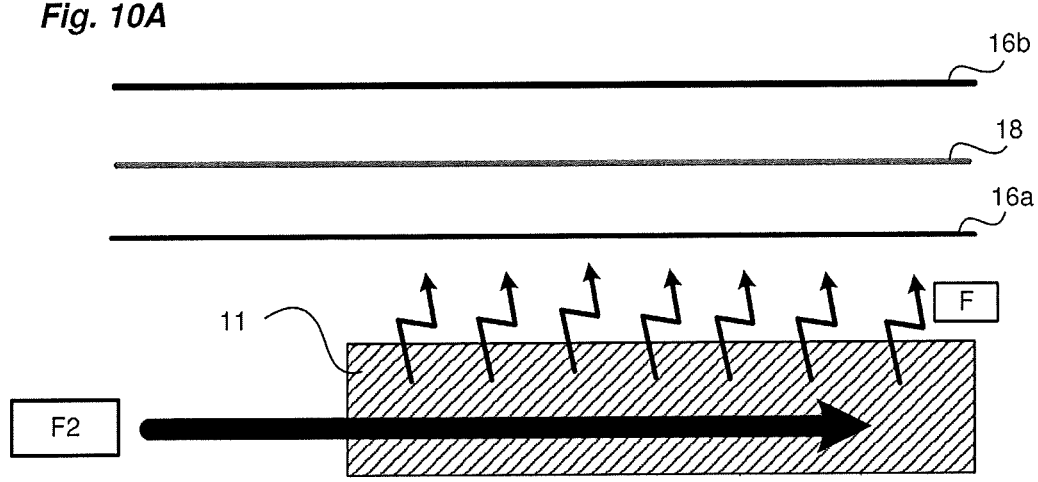
FIGS. 10A and 10B illustrate the fluorescence-recycling principle employed in the device of the invention.
Figure 10B:
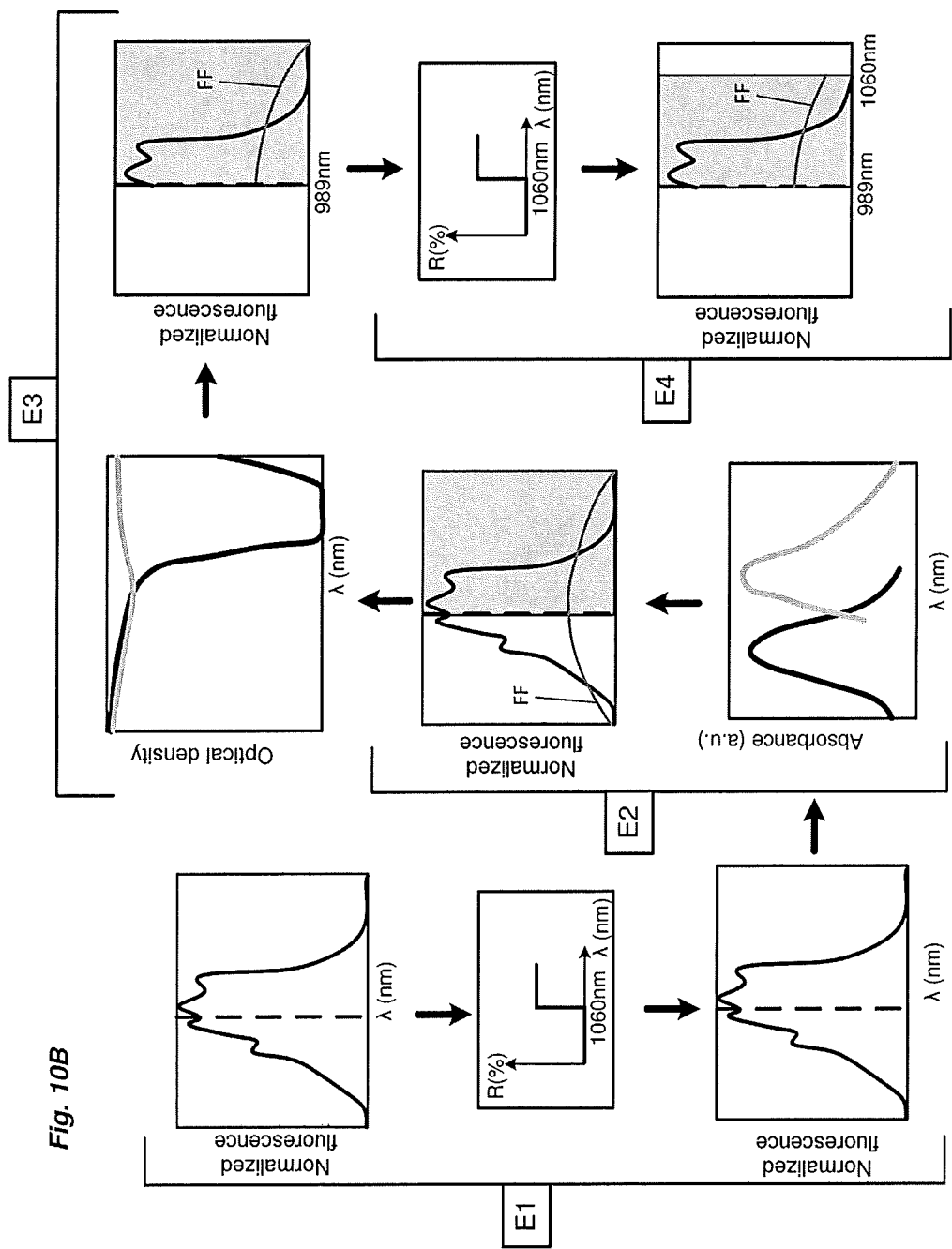

By way of example, FIGS. 10A and 10B thus illustrate the overall principle of recycling of fluorescence that may be employed in the device of the invention:

Step E1: the fluorescence F emitted by the crystal 11 during the excitation by the laser (beam F2) passes through a first dichroic filter 16a. At this stage, the first dichroic filter 16a has no effect on the spectrum.

Step E2: the emitted fluorescence then strikes the fluorophore elements 18. The latter absorb the fluorescence at wavelengths shorter than about 990 nm and reemit fluorescence at wavelengths longer than about 990 nm (grey portion of the graph). The curve referenced FF corresponds to the fluorescence curve of the fluorophore elements.

Step E3: the re-emitted fluorescence passes through the second dichroic filter 16b. This filter then reflects the fluorescence re-emitted by the fluorophore elements 18 at wavelengths longer than 990 nm (grey portion of the graph).

Step E4: the fluorescence reflected by the second dichroic filter 16b once again passes through the first dichroic filter 16a (the fluorophore elements located between the two filters then have no effect). The first dichroic filter 16a then selects the wavelengths to be reinjected into the crystal for recycling. In FIG. 10B, it is a question of the wavelengths comprised between 990 nm and 1060 nm (grey portion of the graph). Specifically, for wavelengths that are beyond 1060 nm, the crystal 11 may start to heat, which would have the inverse effect to that desired.

By virtue of this optical architecture, the light returning to the crystal consists solely of light useful for the optical cooling.

In this optical architecture, the two dichroic filters 16a, 16b and the fluorophore elements 18 will possibly be able to be assembled together in one and the same sheet intended to be arranged around the crystal according to the embodiments described above with reference to FIGS. 5A to 8.

The solution of the invention has many advantages, among which:

presence of a large area of contact between the cooling member and the crystal, allowing heat exchange to be increased;

solution that allows the use of adhesives to fasten the cooling element to the crystal to be avoided, removing the risk of parasitic heating and improving heat exchange between the two elements;

particularly resistant solution, even during the application of thermal operating cycles;

solution that allows a cooling finger of small size to be employed, thus limiting thermal losses to the exterior and allowing the cooling to be optimally localized;

a solution having a high efficiency, in particular by virtue of the use of means for recycling the fluorescence (dichroic filters+fluorophore elements);

a mechanical solution that is reliable and simple to manufacture, by virtue notably of the use of the fastening washer or of the spacers and because the use of adhesives to assemble the elements together is limited; it will be noted that the dichroic-filter covering 16 may be held solely by the cooling member, by virtue of the washer 19, while avoiding any contact between the washer and the crystal and thus allowing any parasitic heating in operation to be avoided.

The invention claimed is:

1. A device for cooling locally, comprising:
a cooling member,
a crystal configured to cool via absorption of a near-infrared exciting light signal,
an illuminating system configured to deliver an exciting light signal, wherein:
said crystal has an elongate shape about a longitudinal axis between a near end and a far end, has a closed constant outside cross section, and contains a central channel formed, from the far end, over at least some of a length of the crystal,
said cooling member comprises a rod embedded via a first end into said central channel of said crystal, and comprises a protruding second end that forms a cooling finger, and
the illuminating system is further configured to generate said exciting light signal with an annular shape.

2. The device according to claim 1, wherein the crystal has a constant cross section of annular shape between the near end and the far end.

3. The device according to claim 1, wherein the illuminating system comprises a light source configured to emit a first light signal, and a shaping module including at least one lens to shape said first light signal, the shaping module being arranged between said light source and the near end of said crystal and configured to generate said exciting signal with the annular shape.

4. The device according to claim 3, wherein the shaping module comprises a first axicon lens and a second axicon lens.

5. The device according to claim 1, wherein the crystal comprises Yb:YLF or Tm:Yb:YLF.

6. The device according to claim 1, wherein the cooling finger of the cooling member has an atraumatic shape.

7. The device according to claim 1, further comprising means for recycling the fluorescence generated during the excitation of said crystal, the means for recycling the fluorescence including one or more filters.

8. The device according to claim 7, wherein said crystal comprises a lateral surface, and wherein the one or more filters comprise one or more dichroic filters that are arranged on the periphery of said lateral surface of the crystal, and that form a lateral covering of said crystal, said covering being thermally insulated from the lateral surface of the crystal.

9. The device according to claim 8, wherein the means for recycling the fluorescence comprise fluorophore elements.

10. The device according to claim 9, wherein said covering comprises at least two of the dichroic filters, and wherein fluorophore elements are arranged between the at least two of the dichroic filters.

11. The device according to claim 9, wherein said covering is composed of a single-piece cylinder or a plurality of adjacent sheets that are assembled with one another in a continuous way.

12. The device according to claim 9, further comprising means for fastening said covering, the means for fastening including a washer.

13. The device according to claim 12, the washer bearing said covering and slipped around the rod of the cooling member.

14. The device according to claim 13, wherein the washer has a face located facing the crystal, on which face is deposited a coating made of reflective material.

15. The device according to claim 14, wherein said means for fastening comprise one or more annular spacers that are positioned around the lateral surface of said crystal and that hold said covering.

16. The device according to claim 15, wherein each spacer comprises a plurality of flexible strips that bear against the lateral surface of said crystal.

* * * * *